United States Patent
Kokubun

(10) Patent No.: US 9,808,174 B2
(45) Date of Patent: Nov. 7, 2017

(54) MAGNETIC-RESONANCE IMAGING DIAGNOSIS APPARATUS AND MAGNETIC-RESONANCE IMAGING METHOD

(75) Inventor: Katsutoshi Kokubun, Tochgi-ken (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1493 days.

(21) Appl. No.: 12/629,582

(22) Filed: Dec. 2, 2009

(65) Prior Publication Data

US 2010/0152568 A1 Jun. 17, 2010

(30) Foreign Application Priority Data

Dec. 16, 2008 (JP) .................................. 2008-319821
Oct. 20, 2009 (JP) .................................. 2009-241712

(51) Int. Cl.
*A61B 5/05* (2006.01)
*A61B 5/055* (2006.01)
(Continued)

(52) U.S. Cl.
CPC .............. *A61B 5/055* (2013.01); *A61B 5/721* (2013.01); *G01R 33/4824* (2013.01);
(Continued)

(58) Field of Classification Search
USPC ......................................... 600/410, 411, 413
See application file for complete search history.

(56) References Cited

U.S. PATENT DOCUMENTS 5,084,818 A * 1/1992 Machida ........................ 324/309
5,611,341 A * 3/1997 Aritomi et al. ............... 600/410
(Continued)

FOREIGN PATENT DOCUMENTS

CN 101017196 A 8/2007
JP 04-292143 A 10/1992
(Continued)

OTHER PUBLICATIONS

Isao Muro, Tomohiko Horie, Eri Kimura, Taichi Matsuo, Yoshisada Ogihara and Akira Hanaki, "Effect of Motion Correction Associated with with Train Length and Number of Blades in PROPELLER MRI-Computer Simulation", Revision acceped Nov. 13, 2003, vol. 60, Issue 2, pp. 264-269 Feb. 2004.

(Continued)

*Primary Examiner* — Amanda Lauritzen Moher
*Assistant Examiner* — Shahdeep Mohammed
(74) *Attorney, Agent, or Firm* — Ken I. Yoshida

(57) ABSTRACT

Upon detecting a body-motion before starting a main-imaging, a sequence-switching control-unit controls operation so as to switch from a usual-imaging sequence to a body-motion adaptive-sequence corresponding to an imaging-portion of a subject P by referring to a body-motion adaptive-sequence storage-unit. Moreover, upon detecting a body-motion during the main-imaging according to the usual-imaging sequence, the sequence-switching control-unit refers to a collected-data storage-unit, and controls operation so as to perform a retake by switching to the body-motion adaptive-sequence if an already-collected data-volume is less than a predetermined volume. By contrast, if the already-collected data-volume is equal to or more than the predetermined volume at a time of detecting a body-motion during the main-imaging, the sequence-switching control-unit stops the main-imaging, and controls a data-processing unit so as to reconstruct a magnetic resonance image only with collected data.

19 Claims, 7 Drawing Sheets

(51) Int. Cl.
*A61B 5/00* (2006.01)
*G01R 33/48* (2006.01)
*G01R 33/565* (2006.01)
*A61B 5/11* (2006.01)
*G01R 33/56* (2006.01)
*G01R 33/561* (2006.01)
*G01R 33/567* (2006.01)

(52) U.S. Cl.
CPC .......... *G01R 33/56509* (2013.01); *A61B 5/11* (2013.01); *G01R 33/561* (2013.01); *G01R 33/5608* (2013.01); *G01R 33/5676* (2013.01)

(56) References Cited

U.S. PATENT DOCUMENTS

| | | | |
|---|---|---|---|
| 6,882,148 B2* | 4/2005 | Pipe | 324/307 |
| 2003/0036693 A1* | 2/2003 | Avinash et al. | 600/413 |
| 2005/0218893 A1* | 10/2005 | Kumai | A61B 5/7257 |
| | | | 324/309 |
| 2007/0088212 A1* | 4/2007 | Takei | A61B 5/055 |
| | | | 600/413 |
| 2007/0205769 A1* | 9/2007 | Yui et al. | 324/318 |
| 2008/0309333 A1* | 12/2008 | Stehning et al. | 324/307 |

FOREIGN PATENT DOCUMENTS

| | | | |
|---|---|---|---|
| JP | 2006-346235 A | | 12/2006 |
| WO | WO2007-072420 | * | 6/2007 |

OTHER PUBLICATIONS

Chinese Office Action dated May 5, 2011 for corresponding CN Application No. 200910225185.5 and English Summary.

* cited by examiner

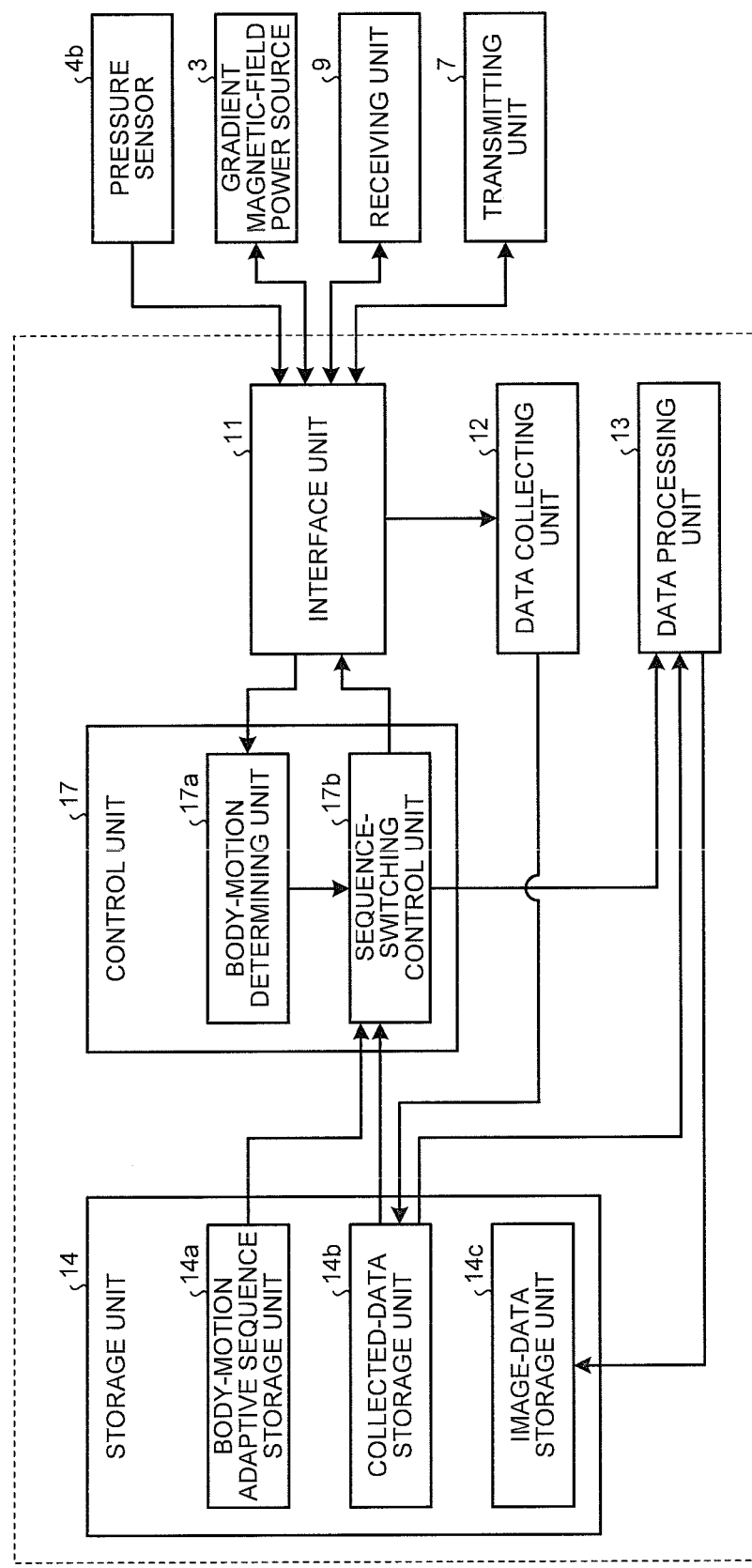

FIG.3

| IMAGING PORTION | BODY-MOTION ADAPTIVE SEQUENCE |
|---|---|
| HEAD | A |
| ABDOMEN | B |
| EXTREMITIES | C |
| PELVIS | D |
| ⋮ | ⋮ |

FIG.4A

USUAL IMAGING SEQUENCE

| DATA COLLECTION VOLUME | OPERATION CONTROL DETAIL WHEN BODY MOTION IS DETECTED |
|---|---|
| LESS THAN 80% | RETAKE BY SWITCHING TO BODY-MOTION ADAPTIVE SEQUENCE |
| 80% OR MORE | DISCONTINUANCE OF IMAGING AND IMAGE RECONSTRUCTION ACCORDING TO ZERO-FILLING METHOD |

FIG.4B

BLADE-ROTATING DATA-COLLECTION SEQUENCE

| IMAGE RECONSTRUCTION BY CREATING k-SPACE DATA IN WHICH BODY MOTION OF SUBJECT IS CANCELLED |
|---|

| IMAGING PORTION | IMAGING INTERVALS [sec] | THRESHOLD [mm] |
|---|---|---|
| HEAD | 60 | 5 |
| NECK | 60 | 10 |
| CHEST | 50 | 15 |
| LUMBAR | 50 | 10 |
| ABDOMEN | 40 | 15 |
| PELVIS | 40 | 10 |
| LOWER EXTREMITY | 30 | 5 |
| UPPER EXTREMITY | 30 | 5 |
| OTHERS | 60 | 10 |

MAGNETIC-RESONANCE IMAGING DIAGNOSIS APPARATUS AND MAGNETIC-RESONANCE IMAGING METHOD

CROSS-REFERENCE TO RELATED APPLICATIONS

This application is based upon and claims the benefit of priority from the prior Japanese Patent Application No. 2008-319821, filed on Dec. 16, 2008 and No. 2009-241712, filed on Oct. 20, 2009; the entire contents of which are incorporated herein by reference.

BACKGROUND OF THE INVENTION

1. Field of the Invention

The present invention relates to a magnetic-resonance imaging diagnosis apparatus and a magnetic-resonance imaging method.

2. Description of the Related Art

Conventionally, according to a magnetic-resonance imaging diagnosis apparatus, a subject placed on a top-plate mat on a couch is fit with a Radio Frequency (RF) coil for local imaging as required, and inserted into the inside of a magnet that includes an opening, and then imaging to take a magnetic resonance image is performed. Specifically, the magnetic-resonance imaging diagnosis apparatus reconstructs an magnetic resonance image by radiating an RF magnetic field onto the subject placed in static magnetic field and collecting Magnetic Resonance (MR) signals emitted from the subject owing to the RF magnetic field, based on a certain data-collecting method (for example, a spin echo method, or a fast spin echo method).

If the subject moves while imaging, an artifact due to the motion is produced on a magnetic resonance image. Such artifact causes difficulty in imaging diagnosis by a doctor with the use of a magnetic resonance image. For this reason, generally an operator of a magnetic-resonance imaging diagnosis apparatus orally tells a subject before imaging not to move during the imaging.

However, despite that imaging is started after orally telling the subject not to move; when determining that it is to take only a magnetic resonance image unavailable for imaging diagnosis because the subject moves during the imaging, the operator discontinues the imaging and then performs a retake under the same conditions. Particularly, when imaging a subject who has difficulty in keeping a steady position due to an advanced age or a disease, a possibility of a retake is high.

To avoid retake, imaging to take a magnetic resonance image is performed by a data collecting method by which motion of a subject can be corrected.

For example, a magnetic resonance image on which motion of a subject is corrected can be reconstructed by using data collected by a method of periodically rotated overlapping parallel lines with enhanced reconstruction (PROPELLER method) (for example, see Isao Muro, et al., "Effect of Motion Correction Associated with Echo Train Length and Number of Blades in PROPELLER MRI-Computer Simulation", Japanese Journal of Radiological Technology, Vol. 60, No. 2, pp. 264-269).

As shown in FIG. 10, the PROPELLER method is a method of collecting k-space data in a frequency region in a non-orthogonal manner by rotating a belt region called "blade", which is formed of a plurality of parallel data collection traces, every repetition time. The PROPELLER method is also called a BLADE method, and hereinafter simply referred to as a "blade-rotating data-collection method", and a pulse sequence according to the "blade-rotating data-collection method" is hereinafter referred to as a "blade-rotating data-collection sequence".

As shown in FIG. 10, according to data collected by the "blade-rotating data-collection sequence", data in the vicinity of the center of the k-space (at which the frequency is "0" in the phase encoding direction and the frequency encoding direction) is present in each blade without exception. Accordingly, by comparing images obtained from data on the k-space through a Fourier transform performed blade by blade, a shift amount between the images corresponding to respective blades in different time sequences can be determined. FIG. 10 is a schematic diagram for explaining the blade-rotating data-collection method.

Based on the determined shift amount, deviations between the images are corrected by relative rotational shift and parallel shift, and a Fourier transform is again performed on k-space data created through an inverse Fourier transform from images corresponding to respective corrected blades, so that a magnetic resonance image can be reconstructed on which influence of motion is suppressed, i.e., artifacts caused by motion of a subject are suppressed.

According to the conventional "blade-rotating data-collection method" described above, because k-space data in a frequency region is filled by overlapping, an imaging time tends to be long. In other words, if imaging is performed by the "blade-rotating data-collection method" from the beginning in order to avoid difficulty in an imaging diagnosis by a doctor, an imaging time for each individual subject tends to be long, resulting in a problem that the imaging diagnosis becomes inefficient.

SUMMARY OF THE INVENTION

According to an aspect of the present invention, a magnetic-resonance imaging diagnosis apparatus includes a data-collection control unit that controls operation so as to take a magnetic resonance image by collecting magnetic resonance signals from an inside of a subject in accordance with a predetermined data-collecting method, and controls operation so as to collect the magnetic resonance signals by switching from the predetermined data-collecting method to a second data-collecting method when a motion of the subject is detected, the second data-collecting method being one of a data collecting method of which an imaging time is shorter than an imaging time of the predetermined data-collecting method and a data collecting method by which motion of the subject can be corrected; and an image reconstructing unit that reconstructs the magnetic resonance image from the magnetic resonance signals that are collected in accordance with a data collecting method executed under control of the data-collection control unit.

According to another aspect of the present invention, a magnetic-resonance imaging method includes controlling operation so as to take a magnetic resonance image by collecting magnetic resonance signals from an inside of a subject in accordance with a predetermined data-collecting method, and controlling operation so as to collect the magnetic resonance signals by switching from the predetermined data-collecting method to a second data-collecting method when a motion of the subject is detected, the second data-collecting method being one of a data collecting method of which an imaging time is shorter than an imaging time of the predetermined data-collecting method and a data collecting method by which motion of the subject can be corrected; and reconstructing the magnetic resonance image from the magnetic resonance signals that are collected in accordance with the executed data collecting method.

BRIEF DESCRIPTION OF THE DRAWINGS

FIG. 2 is a functional block diagram of a detailed configuration of a computer system according to the embodiment;

FIG. 3 is a schematic diagram for explaining a body-motion adaptive sequence storage unit;

FIGS. 4A and 4B are schematic diagrams for explaining a sequence-switching control unit;

DETAILED DESCRIPTION OF THE INVENTION

Exemplary embodiments of a magnetic-resonance imaging diagnosis apparatus and a magnetic resonance imaging method according to the present invention will be explained below in detail with reference to the accompanying drawings. The following description explains as an embodiment a magnetic-resonance imaging diagnosis apparatus that executes a magnetic resonance imaging method according to an embodiment of the present invention.

Figure 1:
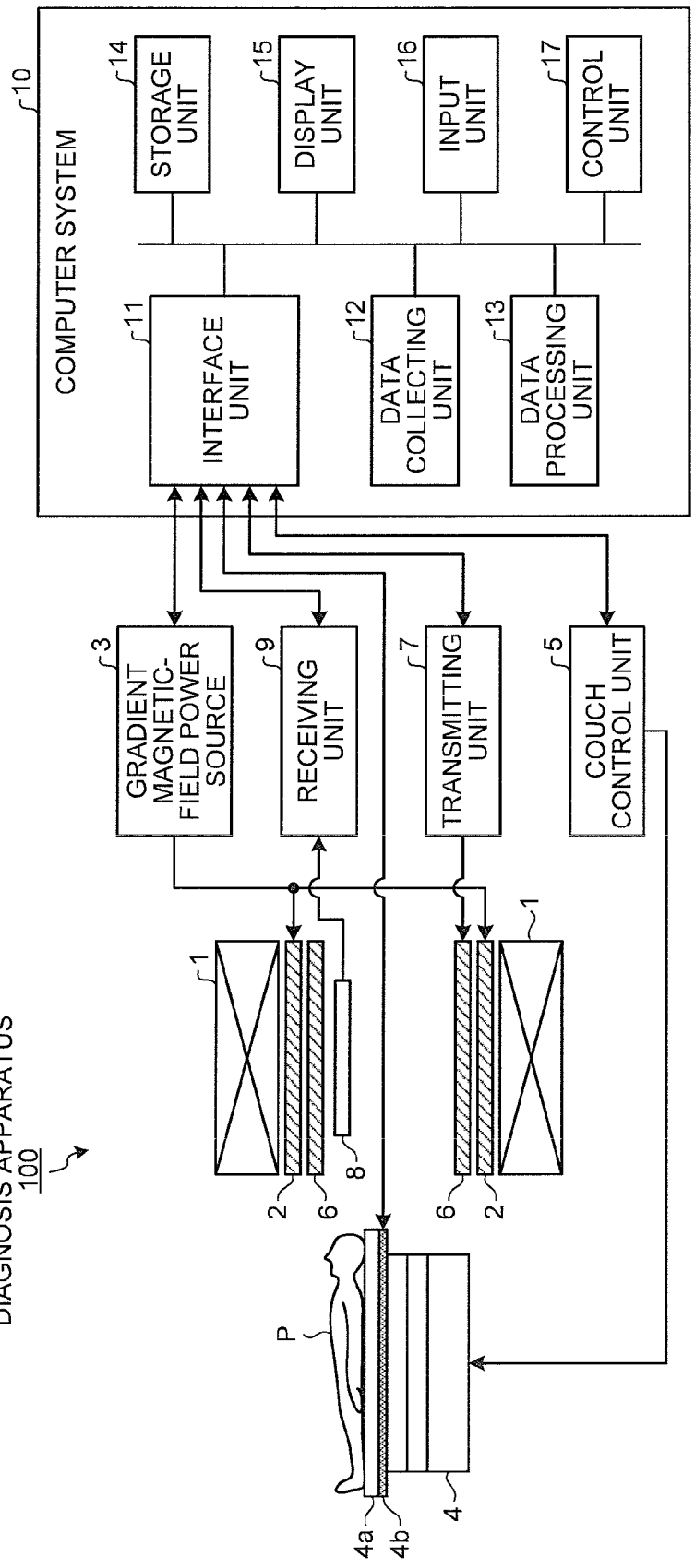
FIG. 1 is a schematic diagram for explaining a configuration of a magnetic-resonance imaging diagnosis apparatus according to an embodiment of the present invention.

First of all, a configuration of a magnetic-resonance imaging diagnosis apparatus according to an embodiment of the present invention is explained below. FIG. 1 is a schematic diagram for explaining a configuration of the magnetic-resonance imaging diagnosis apparatus according to the embodiment. As shown in FIG. 1, a magnetic-resonance imaging diagnosis apparatus 100 according to the embodiment includes a static magnetic-field magnet 1, a gradient magnetic-field coil 2, a gradient magnetic-field power source 3, a couch 4, a couch control unit 5, a Radio Frequency (RF) transmitting coil 6, a transmitting unit 7, an RF receiving coil 8, a receiving unit 9, and a computer system 10.

The static magnetic-field magnet 1 is a magnet formed in a hollow drum shape, and made of a magnet, for example, a permanent magnet or a super conducting magnet. The static magnetic-field magnet 1 generates a uniform static magnetic field in a space inside the drum in which a subject P is to be placed, with a current supplied from a not-shown static magnetic-field power source.

The gradient magnetic-field coil 2 is a coil formed in a hollow drum shape, and is arranged inside the static magnetic-field magnet 1. The gradient magnetic-field coil 2 is formed of three coils in combination corresponding to x, y, and z axes orthogonal to one another, and the three coils generate respective gradient magnetic fields of which magnetic field strengths vary along the x, y, and z axes, respectively, by individually receiving a current supply from the gradient magnetic-field power source 3, which will be described later. It is assumed that the z axis direction is the same direction as that of the static magnetic field.

The gradient magnetic-field power source 3 is a device that supplies a current to the gradient magnetic-field coil 2 based on a set pulse sequence (described later) sent from the computer system 10.

The couch 4 is a device that includes a top plate 4a on which the subject P is to be placed, and under the control of the couch control unit 5, which will be described later, the top plate 4a on which the subject P is placed is inserted into a hole (a scanning space) of the gradient magnetic-field coil 2. Usually, the couch 4 is installed such that the longitudinal direction of the couch 4 is to be parallel to the central axis of the static magnetic-field magnet 1.

As shown in FIG. 1, the top plate 4a is attached with a pressure sensor 4b, and the pressure sensor 4b detects a pressure applied onto the top plate 4a. The pressure sensor 4b will be described later in detail.

The couch control unit 5 is a device that controls the couch 4, and moves the top plate 4a in the longitudinal direction and upward and downward by driving the couch 4.

The RF transmitting coil 6 is a coil arranged inside the gradient magnetic-field coil 2, and generates a radio-frequency magnetic field with a radio-frequency pulse supplied from the transmitting unit 7.

The transmitting unit 7 is a device that transmits a radio-frequency pulse corresponding to a Larmor frequency to the RF transmitting coil 6 based on a set pulse sequence (described later) sent from the computer system 10, and includes an oscillating unit, a phase selecting unit, a frequency converting unit, an amplitude modulating unit, and a radio-frequency power amplifying unit.

The oscillating unit generates a radio-frequency signal of a resonance frequency unique to a subject nucleus in the static magnetic field. The phase selecting unit selects a phase of the radio-frequency signal. The frequency converting unit converts the frequency of a radio-frequency signal output by the phase selecting unit. The amplitude modulating unit modulates amplitude of a radio-frequency signal output by the frequency converting unit in accordance with, for example, a sinc function. The radio-frequency power amplifying unit amplifies a radio-frequency signal output by the amplitude modulating unit. As a result of operations of the above units, the transmitting unit 7 transmits a radio-frequency pulse corresponding to a Larmor frequency to the RF transmitting coil 6.

The RF receiving coil 8 is a coil arranged inside the gradient magnetic-field coil 2, and receives a magnetic resonance signal radiated from the subject owing to an influence of the RF magnetic field. Upon receiving a magnetic resonance signal, the RF receiving coil 8 outputs the received magnetic resonance signal to the receiving unit 9.

The receiving unit 9 is a device that creates magnetic resonance signal data by performing frequency conversion and analog-to-digital (A/D) conversion on a magnetic resonance signal output by the RF receiving coil 8 based on a set pulse sequence (described later) sent from the computer system 10, and transmits the created magnetic resonance signal data to the computer system 10.

The computer system 10 is a device that performs overall control of the magnetic-resonance imaging diagnosis apparatus 100, data collection, image reconstruction, and the like, and includes an interface unit 11, a data collecting unit 12, a data processing unit 13, a storage unit 14, a display unit 15, an input unit 16, and a control unit 17, as shown in FIG. 1.

The interface unit 11 is connected to the gradient magnetic-field power source 3, the couch control unit 5, the transmitting unit 7, and the receiving unit 9; and is a processing unit that controls input and output of signals that are given and received between each of the connected units and the computer system 10.

The data collecting unit 12 is a processing unit that collects magnetic resonance signal data transmitted from the receiving unit 9 via the interface unit 11, and creates k-space data by arranging the collected magnetic resonance signal data in the k-space. The data collecting unit 12 stores the k-space data into the storage unit 14.

The data processing unit 13 is a processing unit that reconstructs image data (magnetic resonance image) by performing post-processing, i.e., reconstruction processing, such as a Fourier transform, on the k-space data stored by the storage unit 14.

The storage unit 14 is a storage unit that stores k-space data received from the data collecting unit 12, and a magnetic resonance image reconstructed by the data processing unit 13, with respect to each of the subject P.

The display unit 15 displays thereon various information, such as a magnetic resonance image, under the control of the control unit 17, and is a monitor device, such as a cathode ray tube (CRT) display, or a liquid crystal display.

The input unit 16 receives various operations and information input from an operator; includes a pointing device, such as a mouse or a trackball, a keyboard, and the like; and cooperates with the display unit 15 to provide a user interface for receiving various operations to the operator of the magnetic-resonance imaging diagnosis apparatus 100.

The control unit 17 includes a Central Processing Unit (CPU) and a memory, both of which are not shown, and is a processing that controls the magnetic-resonance imaging diagnosis apparatus 100 overall.

Specifically, the control unit 17 creates a pulse sequence from various imaging parameters (slice position, slice direction, the number of slices, slice thickness, repetition time, echo time, and the like) according to a data collecting method (for example, a spin echo method or a fast spin echo method) input by an operator via the input unit 16. When an imaging start instruction is input by the operator via the input unit 16, the control unit 17 then causes the gradient magnetic-field power source 3, the transmitting unit 7, and the receiving unit 9 to execute imaging to take a magnetic resonance image by transmitting the created pulse sequence as a set pulse sequence to the gradient magnetic-field power source 3, the transmitting unit 7, and the receiving unit 9 via the interface unit 11.

In this way, the magnetic-resonance imaging diagnosis apparatus 100 according to the embodiment has a main feature that when taking an magnetic resonance image by collecting magnetic resonance signals emitted from the inside of a subject in accordance with a set pulse sequence, processing performed by the control unit 17, which is explained below in detail, ensures that a magnetic resonance image on which artifacts caused by motion of the subject are suppressed is securely taken, thereby being capable to improve the efficiency of an imaging diagnosis. The main feature is explained below with reference to FIGS. 2 to 4. FIG. 2 is a functional block diagram of a detailed configuration of a computer system according to the embodiment; FIG. 3 is a schematic diagram for explaining a body-motion adaptive sequence storage unit; and FIGS. 4A and 4B are schematic diagrams for explaining a sequence-switching control unit.

FIG. 2 depicts a configuration particularly relevant to the present invention from among configurations included in the control unit 17 and the storage unit 14, and interrelation between signals that are exchanged between the interface unit 11, the data collecting unit 12, the data processing unit 13, the storage unit 14, the control unit 17, the pressure sensor 4b, the gradient magnetic-field power source 3, the transmitting unit 7, and the receiving unit 9.

As shown in FIG. 2, the storage unit 14 includes a body-motion adaptive sequence storage unit 14a, a collected-data storage unit 14b and an image-data storage unit 14c.

The collected-data storage unit 14b stores k-space data that is collected and arranged in the k-space by the data collecting unit 12. The image-data storage unit 14c stores a magnetic resonance image created by the data processing unit 13 through reconstruction processing.

The body-motion adaptive sequence storage unit 14a stores a body-motion adaptive sequence referred by a sequence-switching control unit 17b, which will be described later, with respect to each imaging portion. Where it is assumed that a usual imaging sequence is a set pulse sequence created based on imaging parameters input by the operator, a body-motion adaptive sequence is a pulse sequence according to a data collection method of which the imaging time is shorter than that of the usual imaging sequence, or a pulse sequence according to a data collection method by which motion of the subject P can be corrected.

For example, a sequence among body-motion adaptive sequences capable to reduce the imaging time to be shorter than that through the usual imaging sequence by rapidly collecting data can be a pulse sequence according to a "echo planer imaging method" of filling the k-space in a manner of drawing with a single stroke of a brush by rapidly switching a gradient magnetic field in the phase encoding gradient direction and a gradient magnetic field in the frequency encoding gradient direction, when collecting magnetic resonance signals.

Moreover, another sequence among body-motion adaptive sequences capable to reduce the imaging time to be shorter than that through the usual imaging sequence by reducing a data collection volume can be a pulse sequence according to a "half-Fourier method" of collecting magnetic resonance signals that fill only a half of the k-space based on characteristics by which uncollected magnetic resonance signals can be compensated according to Hermitian symmetry. In addition to this, another sequence among body-motion adaptive sequences capable to reduce the imaging time can be a pulse sequence according to a fast field echo method or a spiral fast imaging method.

Moreover, another sequence among body-motion adaptive sequences capable to detect motion of the subject P can be a "blade-rotating data-collection sequence" that is a pulse sequence according to a "blade-rotating data-collection method" of collecting k-space data in a frequency region in a non-orthogonal manner by rotating a belt region called "blade", which is formed of a plurality of parallel data collection traces, every repetition time.

In this way, a body-motion adaptive sequence is preliminarily set with respect to each imaging portion by the operator via the input unit 16 as a pulse sequence for adapting to body motion of the subject P, and stored by the body-motion adaptive sequence storage unit 14a.

Accordingly, for example, as shown in FIG. 3, the body-motion adaptive sequence storage unit 14a stores "A" as a body-motion adaptive sequence when an imaging portion is a "head"; stores "B" as a body-motion adaptive sequence when an imaging portion is a "abdomen"; stores "C" as a body-motion adaptive sequence when an imaging portion is "extremities"; and stores "D" as a body-motion adaptive sequence when an imaging portion is a "pelvis". For example, the operator sets "A" and "B" to the "blade-rotating data-collection sequence" described above. Moreover, the operator sets "C" to a pulse sequence according to the echo planar imaging method described above, and sets "D" to a pulse sequence according to the half Fourier method described above.

Although the embodiment is explained above in a case where a body-motion adaptive sequence is set with respect to each imaging portion, the present invention is not limited this, and can be in a case where a body-motion adaptive sequence is set by further associating it with the type of a magnetic resonance image to be taken (T1 weighted image or T2 weighted image), in addition to imaging portion.

Returning to FIG. 2, the control unit 17 includes a body-motion determining unit 17a, and the sequence-switching control unit 17b.

The body-motion determining unit 17a sequentially receives a pressure applied onto the top plate 4a from the pressure sensor 4b via the interface unit 11. The body-motion determining unit 17a then calculates a variation in the pressure each time when receiving a pressure from the pressure sensor 4b; and when the calculated variation is equal to or higher than a threshold, the body-motion determining unit 17a determines that the subject P produces a body motion.

When the body-motion determining unit 17a determines that the subject P produces a body motion, the sequence-switching control unit 17b executes control explained below.

To begin with, in the first case where the body-motion determining unit 17a determines that the subject P produces a body motion before starting a main imaging according to a usual imaging sequence set by the operator, the sequence-switching control unit 17b controls operation so as to switch from the usual imaging sequence to a body-motion adaptive sequence corresponding to an imaging portion of the subject P, by referring to the body-motion adaptive sequence storage unit 14a. Specifically, in the first case, the sequence-switching control unit 17b creates a pulse sequence based on a body-motion adaptive sequence corresponding to an imaging portion of the subject P by referring to the body-motion adaptive sequence storage unit 14a, and transmits the pulse sequence created based on the body-motion adaptive sequence to the gradient magnetic-field power source 3, the transmitting unit 7, and the receiving unit 9 via the interface unit 11 when receiving a main-imaging start instruction.

Before starting a main imaging means a period from when the subject P placed on the top plate 4a is moved into the hole of the gradient magnetic-field coil 2, through "imaging for a positioning image for imaging planning", "input of imaging parameters by referring to the positioning image", and "creation of a set pulse sequence as a usual imaging sequence from the input imaging parameters", until receiving a main-imaging start instruction.

Moreover, also in the second case where a data volume of already collected magnetic resonance signals is less than a predetermined volume at a time point when the body-motion determining unit 17a determines that the subject P produces a body motion during the main imaging according to the usual imaging sequence as the set pulse sequence, the sequence-switching control unit 17b controls operation so as to switch from the usual imaging sequence to the body-motion adaptive sequence corresponding to the imaging portion of the subject P by referring to the body-motion adaptive sequence storage unit 14a.

Specifically, when a body motion of the subject P is detected during the main imaging according to the usual imaging sequence, the sequence-switching control unit 17b refers to the collected-data storage unit 14b that stores k-space data; and then if a data collection volume is, for example, less than 80%, as shown in FIG. 4A, the sequence-switching control unit 17b controls operation so as to stop imaging according to the usual imaging sequence, and to perform a retake by switching to the body-motion adaptive sequence.

Moreover, in the third case where a data volume of already collected magnetic resonance signals is equal to or more than a predetermined volume at a time point when the body-motion determining unit 17a determines that the subject P produces a body motion during the main imaging according to the usual imaging sequence as the set pulse sequence, the sequence-switching control unit 17b stops the main imaging, and controls the data processing unit 13 so as to reconstruct a magnetic resonance image only with collected k-space data.

Specifically, when a body motion of the subject P is detected during the main imaging according to the usual imaging sequence, the sequence-switching control unit 17b refers to the collected-data storage unit 14b that stores k-space data; and then if a data collection volume is, for example, 80% or more, as shown in FIG. 4A, the sequence-switching control unit 17b controls the gradient magnetic-field power source 3, the transmitting unit 7, and the receiving unit 9, via the interface unit 11, so as to stop imaging, and controls the data processing unit 13 so as to create a magnetic resonance image through image reconstruction according to a zero-filling method by which zero is filled in a data-uncollected k-space region.

When k-space data is filled in accordance with the "blade-rotating data-collection sequence" as the set pulse sequence, the sequence-switching control unit 17b controls the data processing unit 13 so as to reconstruct a magnetic resonance image by creating k-space data in which the body motion of the subject P is cancelled, as shown in FIG. 4B.

Specifically, when k-space data is filled in accordance with the "blade-rotating data-collection sequence", the data processing unit 13 creates images of respective blades through a Fourier transform in accordance with the control by the sequence-switching control unit 17b, and then determines a shift amount between the images corresponding to the respective blades by comparing the created images. The data processing unit 13 then calculates correction parameters with which deviations between the images are corrected by relative rotational shift and parallel shift based on the determined shift amount. The data processing unit 13 then performs motion correction on each image by rotational shift and parallel shift based on the calculated correction parameters, and creates k-space data in which the body motion of the subject P is cancelled by performing an inverse Fourier transform on each motion-corrected image. The data processing unit 13 then reconstructs a magnetic resonance image on which artifacts caused by motion of the subject P are suppressed by performing a Fourier transform again on k-space data in which the body motion is cancelled.

Moreover, when k-space data is filled in accordance with a pulse sequence according to the "half Fourier method" as the set pulse sequence, the sequence-switching control unit 17b controls the data processing unit 13 so as to reconstruct a magnetic resonance image by performing compensation processing with the use of Hermitian symmetry on uncollected magnetic resonance signals.

Figure 5:
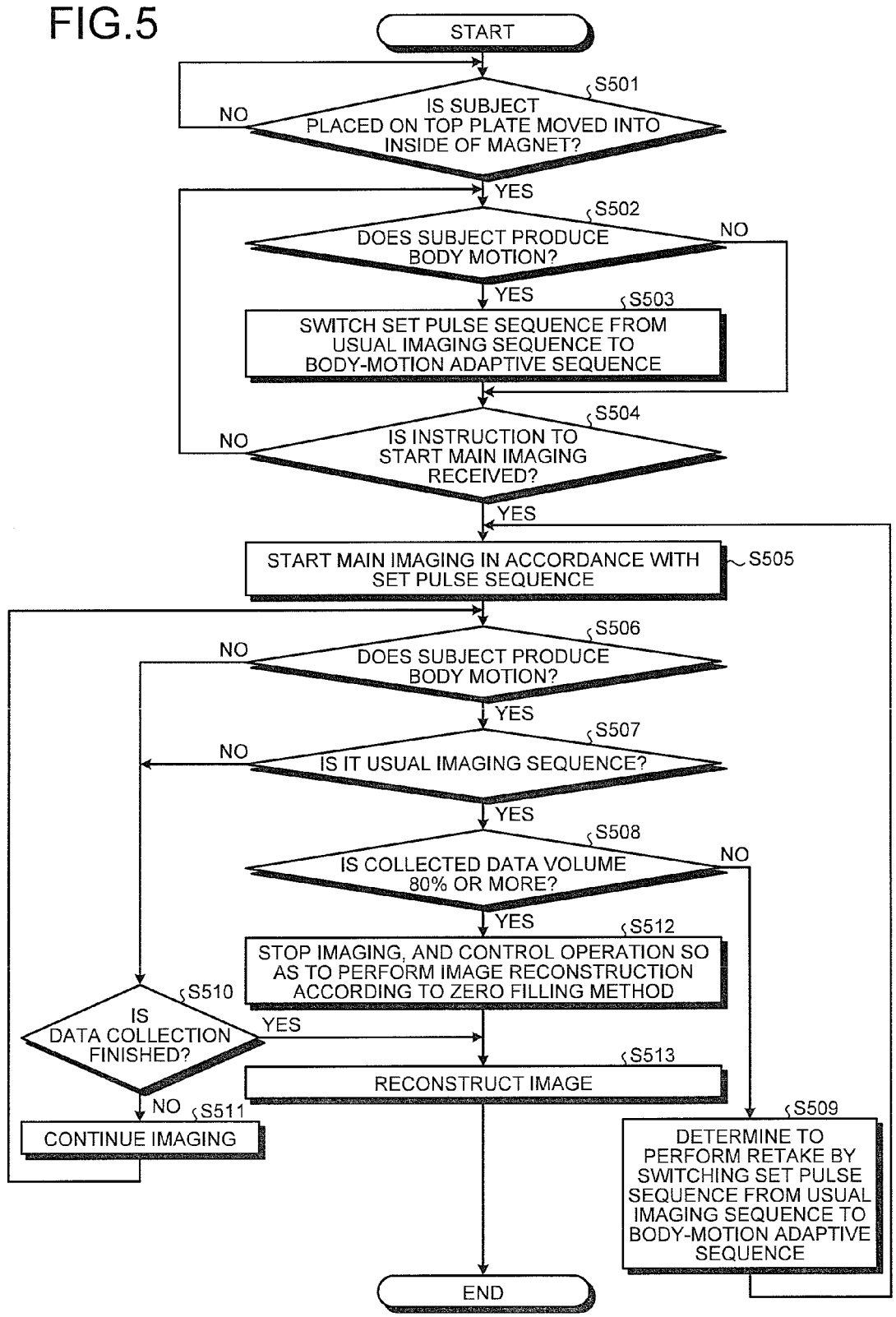
FIG. 5 is a flowchart for explaining processing performed by the magnetic-resonance imaging diagnosis apparatus according to the embodiment.

Processing performed by the magnetic-resonance imaging diagnosis apparatus according to the embodiment is explained below with reference to FIG. 5. FIG. 5 is a flowchart for explaining the processing performed by the magnetic-resonance imaging diagnosis apparatus according to the embodiment.

As shown in FIG. 5, according to the magnetic-resonance imaging diagnosis apparatus 100 according to the embodiment, when the subject P is moved into the inside of the static magnetic-field magnet 1 by the couch control unit 5 in accordance with an instruction by the operator (Yes at Step S501); the body-motion determining unit 17a sequentially receives the pressure applied onto the top plate 4a from the pressure sensor 4b via the interface unit 11, calculates a variation in the pressure, compares the calculated variation with a threshold, and then determines whether the subject P produces body motion (Step S502).

If the body-motion determining unit 17a does not determine that the subject P produces a body motion (No at Step S502), the control unit 17 determines whether an instruction to start a main imaging is received from the operator via the input unit 16 (Step S504); and if the instruction to start the main imaging is not received (No at Step S504), the body-motion determining unit 17a goes back to Step S502, and performs body-motion determination processing of the subject P.

By contrast, if the body-motion determining unit 17a determines that the subject P produces a body motion (Yes at Step S502, the first case), the sequence-switching control unit 17b refers to the body-motion adaptive sequence storage unit 14a, and then controls operation so as to switch from the usual imaging sequence to a body-motion adaptive sequence corresponding to an imaging portion of the subject P (Step S503). Precisely, the sequence-switching control unit 17b creates a pulse sequence based on a body-motion adaptive sequence corresponding to the imaging portion of the subject P, and employs the created pulse sequence as a set pulse sequence.

When the control unit 17 receives the instruction to start the main imaging from the operator via the input unit 16 (Yes at Step S504); the sequence-switching control unit 17b transmits the usual imaging sequence or the body-motion adaptive sequence as a set pulse sequence to the gradient magnetic-field power source 3, the transmitting unit 7, and the receiving unit 9, via the interface unit 11, and causes the main imaging to start in accordance with the set pulse sequence (Step S505).

After that, the body-motion determining unit 17a determines whether the subject P produces body motion, similarly to before starting the main imaging (Step S506); if the subject P does not produce body motion (No at Step S506), the control unit 17 determines whether collection of k-space data is finished (Step S510).

If the collection of k-space data is not finished (No at Step S510), the control unit 17 controls imaging so as to continue the imaging according to the set pulse sequence (Step S511), goes back to Step S506, and controls the body-motion determining unit 17a so as to perform body-motion determination processing of the subject P.

By contrast, if the body-motion determining unit 17a determines that the subject P produces a body motion (Yes at Step S506); and if the set pulse sequence is a body-motion adaptive sequence (No at Step S507); the control unit 17 determines whether collection of k-space data is finished (Step S510). If the collection of k-space data is not finished (No at Step S510), the control unit 17 controls imaging so as to continue the imaging according to the body-motion adaptive sequence (Step S511), goes back to Step S506, and controls the body-motion determining unit 17a so as to perform body-motion determination processing of the subject P.

By contrast, if the body-motion determining unit 17a determines that the subject P produces a body motion (Yes at Step S506); and if the set pulse sequence is the usual imaging sequence (Yes at Step S507); the sequence-switching control unit 17b determines whether a data collection volume of k-space data is 80% or more (Step S508).

If the data collection volume of k-space data is less than 80% (No at Step S508, the second case), the sequence-switching control unit 17b determines that a retake is to be performed by switching the set pulse sequence from the usual imaging sequence to the body-motion adaptive sequence (Step S509), goes back to Step S505, and controls the main imaging to start again in accordance with the set pulse sequence (the body-motion adaptive sequence).

By contrast, if the data collection volume of k-space data is 80% or more (Yes at Step S508, the third case), the sequence-switching control unit 17b stops imaging, and controls the data processing unit 13 so as to perform image reconstruction according to the zero filling method (Step S512), the data processing unit 13 performs image reconstruction according to the zero filling method (Step S513), and then terminates the processing.

As a result of the determination at Step S510, if the collection of k-space data is finished, (Yes at Step S510), the data processing unit 13 performs image reconstruction according to a method corresponding to the usual imaging sequence or the body-motion adaptive sequence based on control by the sequence-switching control unit 17b (Step S513), and then terminates the processing.

When taking a plurality of magnetic resonance images of the same subject, the magnetic-resonance imaging diagnosis apparatus 100 according to the embodiment goes back to Step S502 from immediately before executing image reconstruction processing (or immediately after the image reconstruction processing is performed) at Step S513, and executes again a series of processes described above from the body-motion determination processing of the subject P before imaging.

As described above, according to the embodiment, the body-motion determining unit 17a sequentially receives a pressure applied onto the top plate 4a from the pressure sensor 4b via the interface unit 11, calculates a variation in the pressure, and determines that the subject P produces a body motion if the calculated variation is equal to or higher than a threshold.

In the first case where the body-motion determining unit 17a determines that the subject P produces a body motion before starting a main imaging according to a usual imaging sequence set by the operator, the sequence-switching control unit 17b controls operation so as to switch from the usual imaging sequence to a body-motion adaptive sequence corresponding to an imaging portion of the subject P, by referring to the body-motion adaptive sequence storage unit 14a.

Moreover, in the second case where a data volume of already collected magnetic resonance signals is less than a predetermined volume by referring to the collected-data storage unit 14b at a time point when the body-motion determining unit 17a determines that the subject P produces a body motion during the main imaging according to the usual imaging sequence as the set pulse sequence, the sequence-switching control unit 17b controls operation so as to switch from the usual imaging sequence to the body-motion adaptive sequence corresponding to the imaging portion of the subject P by referring to the body-motion adaptive sequence storage unit 14a and to perform a retake.

Moreover, in the third case where a data volume of already collected magnetic resonance signals is equal to or more than a predetermined volume by referring to the collected-data storage unit 14b at a time point when the body-motion determining unit 17a determines that the subject P produces a body motion during the main imaging according to the usual imaging sequence as the set pulse sequence, the sequence-switching control unit 17b stops the main imaging, and controls the data processing unit 13 so as to reconstruct a magnetic resonance image only with collected k-space data.

Accordingly, even though the imaging time becomes long when the body-motion adaptive sequence is the blade-rotating data-collection sequence, a retake is required only in the second case where a body motion is produced during the main imaging at a stage on which a collected data volume is insufficient for image reconstruction, so that the number of times of retake due to occurrence of body motion can be surely reduced, and as described above in the main feature, the efficiency of an imaging diagnosis can be improved by ensuring that a magnetic resonance image on which artifacts caused by motion of a subject are suppressed is surely taken.

Furthermore, when the subject P produces a body motion, it can be configured to switch automatically to a body-motion adaptive sequence, or to stop imaging automatically and to execute image reconstruction if a collected data volume is sufficient for image reconstruction, accordingly, a burden on to an operator can be reduced.

Although the embodiment is explained above in a case where it is determined whether the subject P produces body motion in accordance with a pressure acquired by the pressure sensor 4b attached to the top plate 4a, the present invention is not limited to this, and can be in cases where whether the subject P produces body motion is determined by four methods explained below.

A first method is a case of observing conditions of the subject P by the operator, thereby determining whether the subject P produces body motion. Precisely, if the operator visually determines that the subject P produces a body motion, the operator presses, for example, a body-motion detection button provided to the input unit 16.

A second method is a case of determining whether the subject P produces body motion by creating a magnetic resonance image from k-space data of the same slice plane collected from the subject P at regular time intervals, and calculating a variation in positional information about a certain portion on the created magnetic resonance image.

For example, before starting a main imaging, a pulse sequence is regulated so as to collect k-space data of the same slice plane at regular time intervals when creating a positioning image for imaging planning; and after the main imaging is started, a set pulse sequence is regulated so as to collect k-space data of the same slice plane at regular intervals.

Accordingly, the data processing unit 13 reconstructs a magnetic resonance image of the same slice plane of the subject P along a time sequence; and the body-motion determining unit 17a extracts a certain portion of the magnetic resonance image, and calculates a variation at coordinates of the certain portion. For example, the body-motion determining unit 17a extracts a head profile and an eye ball from a magnetic resonance image that a head is imaged, and then calculates variations (motion vectors) at coordinates of those portions along a time sequence. When the calculated variation is equal to or higher than a threshold, the body-motion determining unit 17a then determines that the subject P produces a body motion.

A third method is a case of determining whether the subject P produces body motion by detecting motion of a diaphragm by collecting magnetic resonance signals called navigator echoes from a region around the diaphragm when imaging a portion including the diaphragm of the subject P, apart from magnetic resonance signals for imaging. Precisely, the body-motion determining unit 17a identifies the position of the diaphragm by creating one-dimensional data around the diaphragm from navigator echoes, and determines that the subject P produces a body motion if a periodical variation in the identified positions of the diaphragm deviates from a threshold.

A fourth method is a case of determining whether the subject P produces body motion by creating profile data from magnetic resonance signal data of the same slice plane collected from the subject P at regular time intervals, and calculating a variation in positional information about a predetermined portion in the created profile data. The fourth method is explained below with reference to FIGS. 6 to 9. FIGS. 6 to 9 are schematic diagrams for explaining the fourth method.

To begin with, when taking a magnetic resonance image, the sequence-switching control unit 17b causes execution of imaging for body-motion profile data for collecting profile data for determining presence or absence of occurrence of body motion. When executing the imaging, in order to determine presence or absence of body motion precisely, the sequence-switching control unit 17b causes the execution of the imaging for the body-motion profile data so as to collect profile data of a slice plane in the same portion as an imaging portion for a magnetic resonance image. Moreover, the sequence-switching control unit 17b causes the execution of the imaging for the body-motion profile such that the slice plane includes the magnetic field center. When taking a magnetic resonance image, to take a magnetic resonance image of high quality, usually the imaging portion of the subject P is moved to the magnetic field center that is the center of a static magnetic field generated by the static magnetic-field magnet 1. Therefore, through control such that a slice plane of imaging for body-motion profile data includes the magnetic field center, profile data having a high Signal-to-Noise (SN) ratio of the signal strength can be collected.

Figure 6:
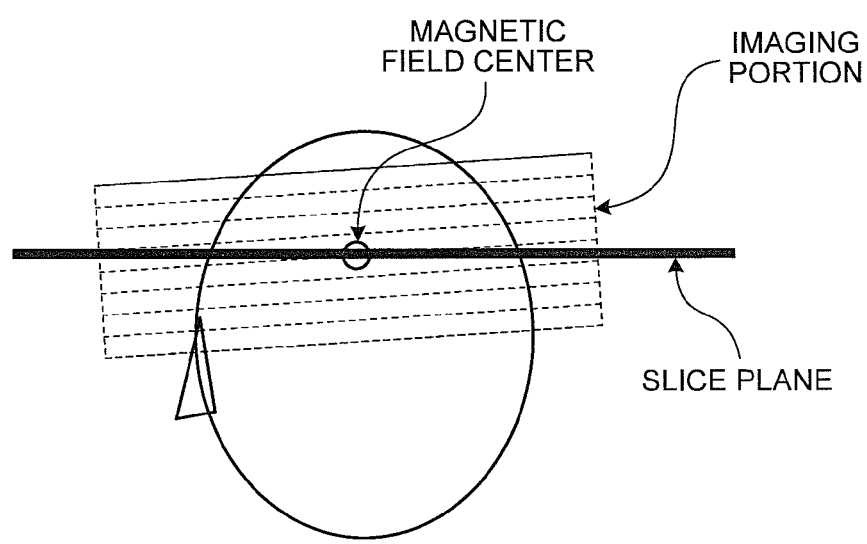
FIGS. 6 to 9 are schematic diagrams for explaining a fourth method.

For example, as shown in FIG. 6, when an imaging portion for a magnetic resonance image is a head of the subject P, the sequence-switching control unit 17b sets in the head a slice plane from which profile data is to be collected such that the slice plane from which profile data is to be collected include the magnetic field center, and causes execution of imaging for body-motion profile data.

Figure 7:
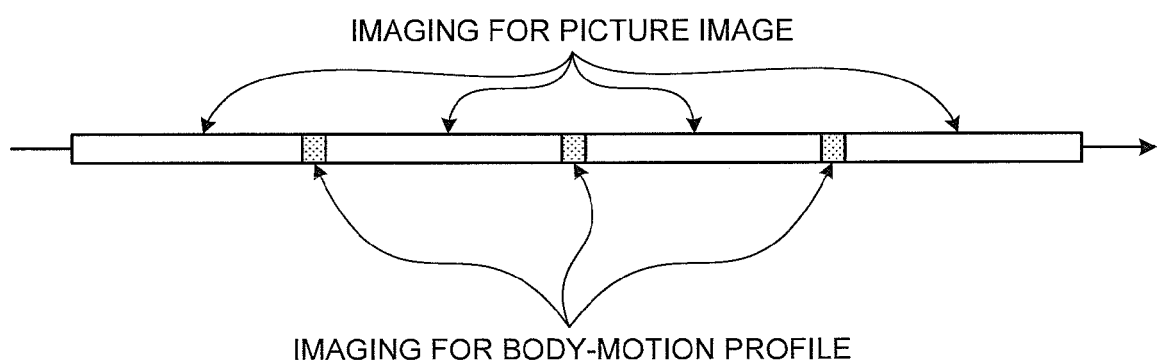

Furthermore, as shown in FIG. 7, the sequence-switching control unit 17b causes execution of imaging for body-motion profile data repeatedly at regular time intervals while taking a magnetic resonance image. For example, the sequence-switching control unit 17b controls imaging for body-motion profile data so as to be executed every 60 seconds. Alternatively, the sequence-switching control unit 17b controls imaging for body-motion profile data so as to be executed each time when a repetition time set in a pulse sequence for imaging to take a picture image has elapsed.

Figure 8:
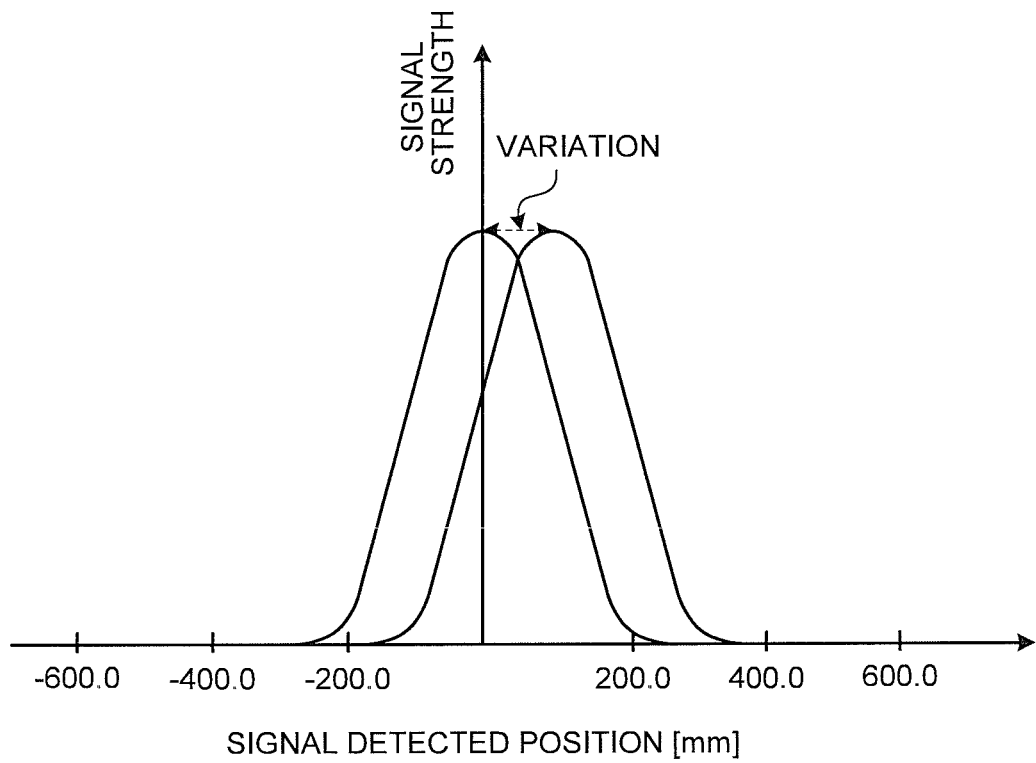

The data processing unit 13 that receives magnetic resonance signal data collected through such imaging for body-motion profile data creates profile data by performing a one-dimensional Fourier transform on the received magnetic resonance signal data. The body-motion determining unit 17*a* then calculates a variation in the sequentially created profile data. For example, as shown in FIG. 8, each time when profile data is created, the body-motion determining unit 17*a* detects a signal-strength detected position at which the signal strength is the maximum, and calculates a variation in the detected signal-strength detected positions. The body-motion determining unit 17*a* then determines that the subject P produces a body motion, for example, when the calculated variation becomes equal to or higher than a threshold that is predetermined.

According to the fourth method, the body-motion determining unit 17*a* can perform body-motion determination by using a table in which imaging intervals and thresholds of imaging for body-motion profile data are set with respect to each imaging portion for a magnetic resonance image. For example, as shown in FIG. 9, when a table is stored in which "imaging portion: head" is associated with "imaging interval: 60 seconds" and "threshold: 5 millimeters"; the sequence-switching control unit 17*b* controls operation so as to execute imaging for body-motion profile data every 60 seconds during imaging of the head; and when a calculated variation becomes 5 millimeters or more, the body-motion determining unit 17*a* determines that the subject P produces a body motion.

Figures 9, 10:
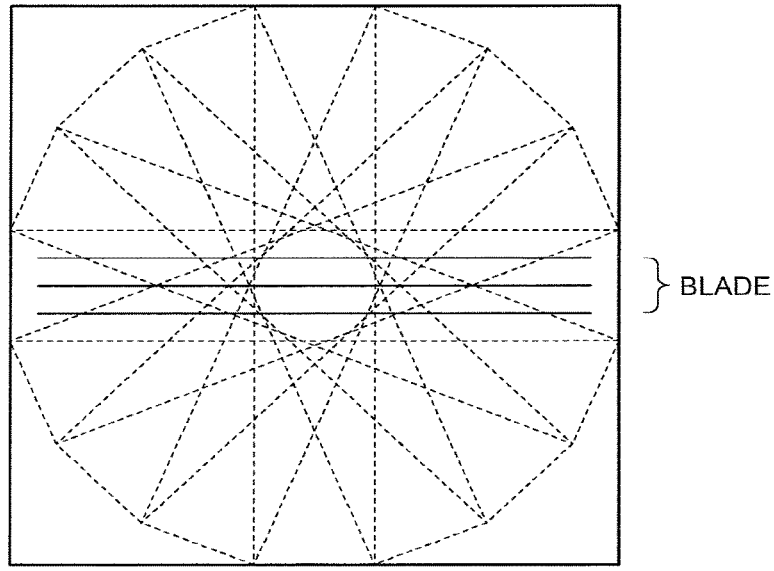
FIG. 10 is a schematic diagram for explaining a blade-rotating data-collection method.

The thresholds shown in FIG. 9 can be set to arbitrary values by an operator of the magnetic-resonance imaging diagnosis apparatus 100 in accordance with an imaging portion. For example, when an imaging portion is a head, the operator sets a threshold to a small value because the operator wants to reduce artifacts on a magnetic resonance image caused by motion of the subject P to a minimum. When an imaging portion is a small portion, such as a lower extremity or an upper extremity, because influence of body motion of the subject P is large, the operator sets a threshold to a small value. In other words, by setting the table as shown in FIG. 9, body-motion determination appropriately to an imaging portion can be performed.

When it is determined that the subject P produces a body motion according to the four methods described above; similarly to the embodiment described above, if before a main imaging, the sequence-switching control unit 17*b* switches the set pulse sequence from a usual imaging sequence to a body-motion adaptive sequence, and if during the main imaging, the sequence-switching control unit 17*b* executes set pulse-sequence switching processing based on a collected k-space data volume, or imaging-discontinuance processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic-resonance imaging diagnosis apparatus comprising:
   a computer;
   a data-collection controller configured to automatically detect a motion of a subject and to control a magnetic resonance image via main imaging by collecting magnetic resonance signals from an inside of the subject, a data collection method being initialized to a first image data-collecting method before collecting the magnetic resonance signals, said data-collection controller controlling to switch the data collection method from the first image data-collecting method to a second image data-collecting method when the motion of the subject is detected and to collect the magnetic resonance signals by the second image data-collecting method after switching the data collection method, the second image data-collecting method being one of a data collecting method having a shorter imaging time than the first image data-collecting method and a data collecting method correcting some of the magnetic resonance signals corresponding to the motion of the subject; and
   said computer connected to said data-collection controller and that reconstructs the magnetic resonance image from the magnetic resonance signals that are collected during the main imaging in accordance with the data collection method,
   wherein a pulse sequence of the first data-collecting method is created based on first imaging parameters of the first image data-collecting method, and a pulse sequence of the second image data-collecting method is created based on second imaging parameters of the second image data-collecting method that are different from those of the first imaging parameters.

2. The magnetic-resonance imaging diagnosis apparatus according to claim 1, wherein the data-collection controller controls to switch from the first image data-collecting method to the second image data-collecting method in a first case where the motion of the subject is detected before the main imaging, and in a second case where a data volume of already collected magnetic resonance signals is less than a predetermined volume at a time point when the motion of the subject is detected during the main imaging according to the first image data-collecting method, and the data-collection controller stops the main imaging in a third case where the data volume of already collected magnetic resonance signals is equal to or more than the predetermined volume at a time point when the motion of the subject is detected during the main imaging according to the first image data-collecting method, and controls said computer so as to reconstruct the magnetic resonance image only with collected magnetic resonance signals.

3. The magnetic-resonance imaging diagnosis apparatus according to claim 2, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

4. The magnetic-resonance imaging diagnosis apparatus according to claim 2, further comprising a storage device configured to store a set of predetermined image data-collecting methods each of which is used as the second image data-collecting method and each of the predetermined image data-collecting methods is associated with at least one of an imaging portion and a type of magnetic resonance image, wherein the data-collection controller retrieves from the storage device one of the predetermined image data-collecting methods as the second image data-collecting method based upon the imaging portion of the subject who is currently being imaged and the type of magnetic resonance image which the subject is currently being imaged as one of the first case and the second case occurs.

5. The magnetic-resonance imaging diagnosis apparatus according to claim 4, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

6. The magnetic-resonance imaging diagnosis apparatus according to claim 2, wherein the data-collection controller detects the motion of the subject from a variation in positional information about a predetermined portion inside the subject based on magnetic resonance signals at the predetermined portion.

7. The magnetic-resonance imaging diagnosis apparatus according to claim 6, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

8. The magnetic-resonance imaging diagnosis apparatus according to claim 6, further comprising a storage device configured to store a set of predetermined image data-collecting methods each of which is used as the second image data-collecting method and each of the predetermined image data-collecting methods is associated with at least one of an imaging portion and a type of magnetic resonance image, wherein the data-collection controller retrieves from the storage device one of the predetermined image data-collecting methods as the second image data-collecting method based upon the imaging portion of the subject who is currently being imaged and the type of magnetic resonance image which the subject is currently being imaged as one of the first case and the second case occurs.

9. The magnetic-resonance imaging diagnosis apparatus according to claim 8, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

10. The magnetic-resonance imaging diagnosis apparatus according to claim 6, wherein the data-collection controller detects the motion of the subject from a variation in positional information about a predetermined portion inside the subject, the variation being calculated from profile data based on magnetic resonance signals at the predetermined portion.

11. The magnetic-resonance imaging diagnosis apparatus according to claim 10, wherein the data-collection controller performs control such that the predetermined portion is to be identical to an imaging portion for the magnetic resonance image.

12. The magnetic-resonance imaging diagnosis apparatus according to claim 11, wherein the data-collection controller performs control such that the predetermined portion includes a magnetic-field center in the imaging portion for the magnetic resonance image.

13. The magnetic-resonance imaging diagnosis apparatus according to claim 12, wherein the data-collection controller controls operation so as to execute imaging for collecting the profile data repeatedly at predetermined time intervals while taking the magnetic resonance image.

14. The magnetic-resonance imaging diagnosis apparatus according to claim 13, further comprising a threshold storage configured to store time intervals and thresholds that are set for respective imaging portions for the magnetic resonance image, wherein the data-collection controller controls operation so as to acquire a time interval out of the time internals and a threshold out of the thresholds associated with an imaging portion for the magnetic resonance image from the threshold storage, and then to execute imaging for collecting the profile data at the acquired time interval, and controls operation so as to compare the acquired threshold with a variation in positional information about the predetermined portion calculated from profile data collected through the imaging executed at the acquired time interval, and then to determine presence or absence of the motion of the subject.

15. The magnetic-resonance imaging diagnosis apparatus according to claim 2, wherein the data-collection controller detects the motion of the subject from a variation in a pressure applied onto a top plate on which the subject is to be placed, the motion being detected by a pressure-sensor attached to the top plate.

16. The magnetic-resonance imaging diagnosis apparatus according to claim 15, further comprising a storage device configured to store a set of predetermined image data-collecting methods each of which is used as the second image data-collecting method and each of the predetermined image data-collecting methods is associated with at least one of an imaging portion and a type of magnetic resonance image, wherein the data- collection controller retrieves from the storage device one of the predetermined image data-collecting methods as the second image data-collecting method based upon the imaging portion of the subject who is currently being imaged and the type of magnetic resonance image which the subject is currently being imaged as one of the first case and the second case occurs.

17. The magnetic-resonance imaging diagnosis apparatus according to claim 16, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

18. The magnetic-resonance imaging diagnosis apparatus according to claim 15, wherein the second image data-collecting method is a method of collecting the magnetic resonance signals by rotating every repetition time a belt-shaped region formed of a plurality of parallel data collection traces in a frequency space, and said computer reconstructs the magnetic resonance image based on a correction parameter for correcting the motion of the subject detected from magnetic resonance signals collected by the second image data-collecting method.

19. A magnetic-resonance imaging method comprising: initializing a data collection method to a first image data-collecting method for main imaging before collecting magnetic resonance signals for main imaging; controlling a magnetic resonance image via the main imaging by collecting magnetic resonance signals from an inside of a subject; automatically detecting a motion of the subject; controlling to switch the data collection method from the first image data-collecting method to a second image data-collecting method when the motion of the subject is detected and to collect the magnetic resonance signals by the second image data-collecting method after switching the data collection method, the second image data-collecting method being one of data collecting method having a shorter imaging time than the first image data-collecting method and a data correcting method correcting some of the magnetic resonance signals corresponding to the motion of the subject; and reconstructing the magnetic resonance image from the magnetic resonance signals that are collected during the main imaging in accordance with the data collection method, wherein a pulse sequence of the first image data-collecting method is created based on first imaging parameters of the first image data-collecting method, and a pulse sequence of the second image data-collecting method is created based on second imaging parameters of the second image data-collecting method that are different from those of the first imaging parameters.

* * * * *